US012766303B2

United States Patent
(12) United States Patent
Ryan

(10) Patent No.: US 12,766,303 B2
(45) Date of Patent: Oct. 20, 2026

(54) SELF-ALIGNING, UNIVERSAL CAP FOR MALE AND FEMALE LUER CONNECTORS

(71) Applicant: Becton, Dickinson and Company, Franklin Lakes, NJ (US)

(72) Inventor: Kevin M. Ryan, Whitehouse Station, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 902 days.

(21) Appl. No.: 18/114,367

(22) Filed: Feb. 27, 2023

(65) Prior Publication Data

US 2024/0285926 A1 Aug. 29, 2024

(51) Int. Cl.

*A61M 39/20* (2006.01)
*A61M 39/10* (2006.01)
*A61M 39/16* (2006.01)

(52) U.S. Cl.

CPC .......... *A61M 39/20* (2013.01); *A61M 39/162* (2013.01); *A61M 2039/1038* (2013.01); *A61M 2205/0205* (2013.01)

(58) Field of Classification Search

CPC ................ A61M 39/20; A61M 39/162; A61M 2039/1077; A61M 2039/1038; A61M 2039/1033; A61M 39/165

See application file for complete search history.

(56) References Cited

U.S. PATENT DOCUMENTS

| | | | | |
|---|---|---|---|---|
| 2016/0067422 A1* | 3/2016 | Davis | A61M 5/3134 604/192 |
| 2019/0234540 A1* | 8/2019 | Marici | A61M 39/165 |
| 2021/0322749 A1 | 10/2021 | Rothenberg et al. | |
| 2021/0322750 A1* | 10/2021 | Harandi | A61M 39/162 |
| 2022/0273931 A1 | 9/2022 | Jiang et al. | |

OTHER PUBLICATIONS

"PCT International Search Report and Written Opinion in PCT/US2024/017214 dated Jul. 4, 2024, 12 pages".

* cited by examiner

*Primary Examiner* — Courtney Fredrickson
*Assistant Examiner* — Kayla M. Turkowski
(74) *Attorney, Agent, or Firm* — Servilla Whitney LLC

(57) ABSTRACT

A universal cap for connection to medical connectors facilitates easier cap alignment and engagement with threaded male or female Luer medical connectors and enhanced connector disinfection. A split-collar protrusion projects axially from a closed end wall of the cap towards the open bottom and comprises at least an opposed pair of parallel, sector-shaped, collet fingers/prongs that terminate in protrusion tips. The inner wall of each collet finger respectively defines a split-flange cantilever. Inner and outer walls of each collet finger define split threads, which are respectively sized for mating engagement with respective corresponding threads of Luer connectors. An antibacterial infused absorbent material is oriented between the split flanges and the cap bottom. As the cap is affixed to a Luer connector, absorbent material compression biases the split flanges and deflects the collet fingers/prongs, for easier cap alignment and engagement with Luer medical connectors and enhanced connector disinfection.

13 Claims, 8 Drawing Sheets

SELF-ALIGNING, UNIVERSAL CAP FOR MALE AND FEMALE LUER CONNECTORS

TECHNICAL FIELD

The present disclosure generally relates to a device for disinfecting and sterilizing access ports with, e.g., male and/or female Luer fittings, and, in particular, to disinfecting and sterilizing devices capable of accommodating multiple types of Luer connectors. Generally, exemplary embodiments of the present disclosure relate to the fields of threaded fitting, including medical caps and medical disinfection caps, and in particular universal application medical caps and/or disinfection caps for uses with either or both of male and female, fluid Luer connectors.

BACKGROUND

Vascular access devices (VAD's) are commonly used therapeutic devices and include intravenous (IV) catheters. There are two general classifications of VAD's: peripheral catheters and central venous catheters. Bacteria and other microorganisms may gain entry into a patient's vascular system from access hubs and ports/valves upon connection to the VAD to deliver the fluid or pharmaceutical. Each access hub (or port/valve or connection) is associated with some risk of transmitting a catheter related bloodstream infection (CRBSI), which can be costly and potentially lethal.

In order to decrease CRBSI cases and to ensure VAD's are used and maintained correctly, standards of practice have been developed, which include disinfecting and cleaning procedures.

Disinfection caps have been added to the Society for Healthcare Epidemiology of America (SHEA) guidelines and early indications are that caps will also be incorporated into the 2016 Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Currently, caps for male needleless connectors, female needleless connectors, intravenous (IV), and hemodialysis lines use different designs and are, therefore, limited to the types of connectors to which the cap can be attached. Currently, there are male disinfecting cap devices for disinfecting ISO594-2 type of female threaded fluid luer connectors and there are female disinfecting cap devices for disinfecting ISO594-2 type of male threaded fluid luer connectors. Thus, prior disinfecting caps were designed to fit one type of connector only, and were specific to one particular size and/or shape of connector.

U.S. Pat. No. 11,511,100 discloses a singular universal disinfecting cap device with features allowing it to interface with either a male or female type of threaded connectors. FIGS. 1 and 2 correspond to the structural illustrations of respective FIGS. 7 and 10 of U.S. Pat. No. 11,511,100, but with different reference numbers and lead lines. In FIGS. 1 and 2, a cap 10 comprises a housing 12, which includes an inner sidewall 14 and an axial wall 16 defining a first cavity 18, and an open bottom 20 into the first cavity 18. From the wall 16 extends a protrusion 22 (which can be essentially cylindrical and coaxial with inner sidewall 14) having an inner surface 24 defining a second cavity 26, and a tapered outer surface 28 defining an outer portion of the first cavity 18. The protrusion 22 comprises an inner thread 30 on its inner surface 24 for engaging a female Luer connector and the outer surface 28 being tapered, sized and adapted to engage a male Luer connector in a press-fit connection sufficient to interlock with a mating feature of said male needleless connector. The protrusion 22 is illustrated as comprising two prongs 32 spaced by cutouts or gaps 34 and extending essentially from the distal wall 16 in a proximal direction.

Referring to FIG. 2, in one or more embodiments, an absorbent material 36 is disposed within the chamber defined by the first cavity 18 and second cavity 26, the absorbent material being under radial compression by the inner thread 30 on the inner surface 24 of protrusion 22 to retain the absorbent material 36 in the first cavity 18 and second cavity 26. As shown in FIG. 2, in one or more embodiments, the absorbent material 36 comprises an inner cylindrical material 38 and an outer cylindrical material 40. The inner cylindrical material 38 is disposed within the second cavity 26, and the outer cylindrical material 40 being disposed within the first cavity 18, the outer cylindrical material 40 being a ring having an aperture and an aperture diameter essentially equal to the outer diameter of the protrusion 22, so that the outer cylindrical material 40 is disposed only within the first cavity 18, being in contact with the inner sidewall 14 of the housing 12 and the outer surface 28 of the protrusion 22. The absorbent material 36, the inner cylindrical material 38 and outer cylindrical material 40 abut the axial end wall 16 when placed within the first cavity 18 or second cavity 24.

SUMMARY

Embodiments of the disclosure pertain to a universal cap for connection to and disinfection of a medical connector, including male connectors and female connectors. The universal cap embodiments disclosed herein facilitate easier cap alignment and engagement with threaded male or female Luer medical connectors and enhanced connector disinfection. A split-collar protrusion projects axially from a closed end wall of the cap towards the open bottom and comprises at least an opposed pair of parallel, sector-shaped, collet fingers/prongs that terminate in protrusion tips. Some cap embodiments have more than two collet fingers/prongs. The inner wall of each collet finger/prong of the split-collar protrusion respectively defines a split-flange cantilever. Each split flange has a flange root that is coupled to its corresponding inner wall, from which projects an axial contact surface that terminates in a flange tip. Collectively, the respective flange tips of the split flanges are in radially inwardly opposed orientation with respect to an axial centerline of the split-collar protrusion, and commonly oriented axially along the protrusion inner wall, intermediate the closed end wall and the protrusion tips. While two collet fingers/prongs 61 are shown in this cap 50 embodiment, other embodiments incorporate more than two of them. Inner and outer walls of each collet finger/prong respectively define split inner and outer threads, which are respectively sized for mating engagement with respective corresponding female and male threads of Luer connectors. An absorbent material is oriented between the split flanges and the cap bottom. In some embodiments, the absorbent material is infused with an antimicrobial agent. As the cap is affixed to a Luer connector, compression of the absorbent material biases the split flanges toward the cap end wall and deflects the tips of the collet fingers/prongs radially inwardly, toward the cap's axial centerline, for easier cap alignment and engagement with the corresponding connector and enhanced connector disinfection. The exemplary cap disclosed herein provides a mechanical barrier for medical connectors and retains the antimicrobial agent for disinfection. The cap of the present disclosure allows the medical practitioner to streamline the disinfection process by simplifying cap/connector engagement while simultaneously disinfecting the connector.

One aspect of the present disclosure pertains to a cap for coupling to a male or female Luer medical connector. The cap comprises a housing having an axial centerline. The cap defines a first cavity formed within a housing top wall and a circumscribing housing sidewall. The cavity is in communication with an open bottom of the housing. A split-collar protrusion is oriented within the first cavity, coupled to the top wall, circumscribing the axial centerline and projecting toward the open bottom. This protrusion has a plurality of opposed, parallel, sector-shaped, collet prongs, also referred to as collet fingers. Each respective collet finger/prong has a distal protrusion tip and a protrusion outer wall surface, which defines outer wall split threads that are sized and adapted for mating engagement with corresponding collar threads of a male Luer connector. Each respective collet finger/prong also has an inner wall surface defining inner wall split threads that are sized and adapted for mating engagement with corresponding threads of a female Luer connector. The respective inner wall split threads and the respective outer wall split threads start at the distal protrusion tip and terminate proximate the top wall. The respective inner surfaces of the collet prongs define a second cavity sized and adapted for receipt of a male or a female Luer connector. A split flange is coupled to the inner wall surface of each respective collet prong by a flange root, intermediate the inner split threads and the top wall. Each separate, respective split flange has a cantilever-like, distal axial contact surface that is commonly oriented radially inwardly with respect to the axial centerline of the housing and terminates in a flange tip that is radially opposed to the other flange tips. An absorbent material is interposed within the second cavity, between the respective split flanges and the open bottom of the housing, The absorbent material compresses during advancement of a male or a female Luer connector within the second cavity and biases the split flanges toward the top wall of the housing. The now biased split flanges deflect the protrusion tip of its respective collet prong inwardly toward the axial centerline of the housing.

This summary is provided to introduce a selection of concepts in a simplified form that are further described below in the Detailed Description. Additional features and advantages of the disclosure are set forth in the description, below and in the appended claims.

BRIEF DESCRIPTION OF THE DRAWINGS

Exemplary embodiments of the disclosure are further described in the following detailed description in conjunction with the accompanying drawings, in which.

To facilitate understanding, identical reference numerals have been used, where possible, to designate identical elements that are common to the figures. The figures are not drawn to scale.

DETAILED DESCRIPTION

Figure 1:
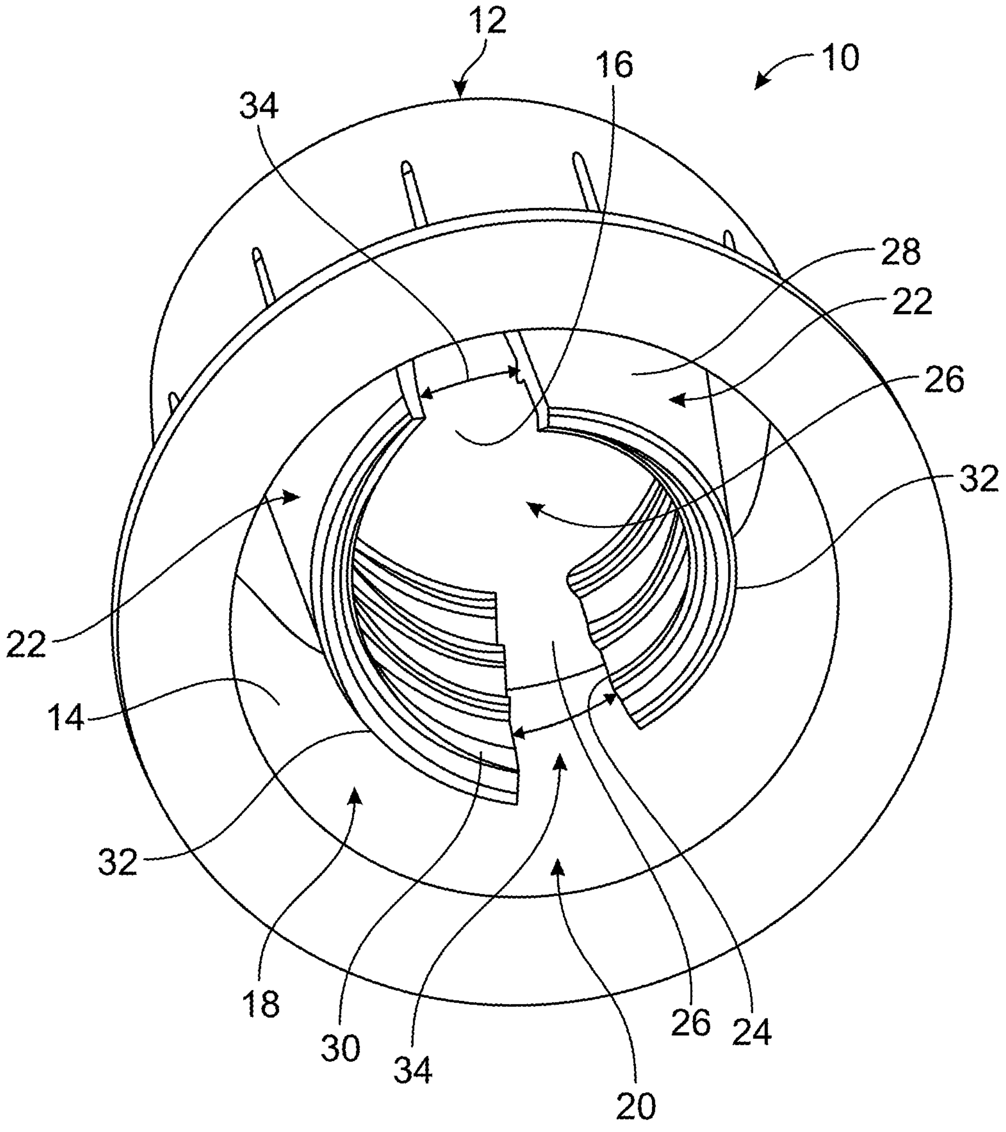
FIG. 1 (PRIOR ART)
FIG. 1 is an isometric view of an embodiment of a universal cap for coupling to either male or female Luer connectors, which corresponds to FIG. 7 of U.S. Pat. No. 11,511,100.
Figure 2:
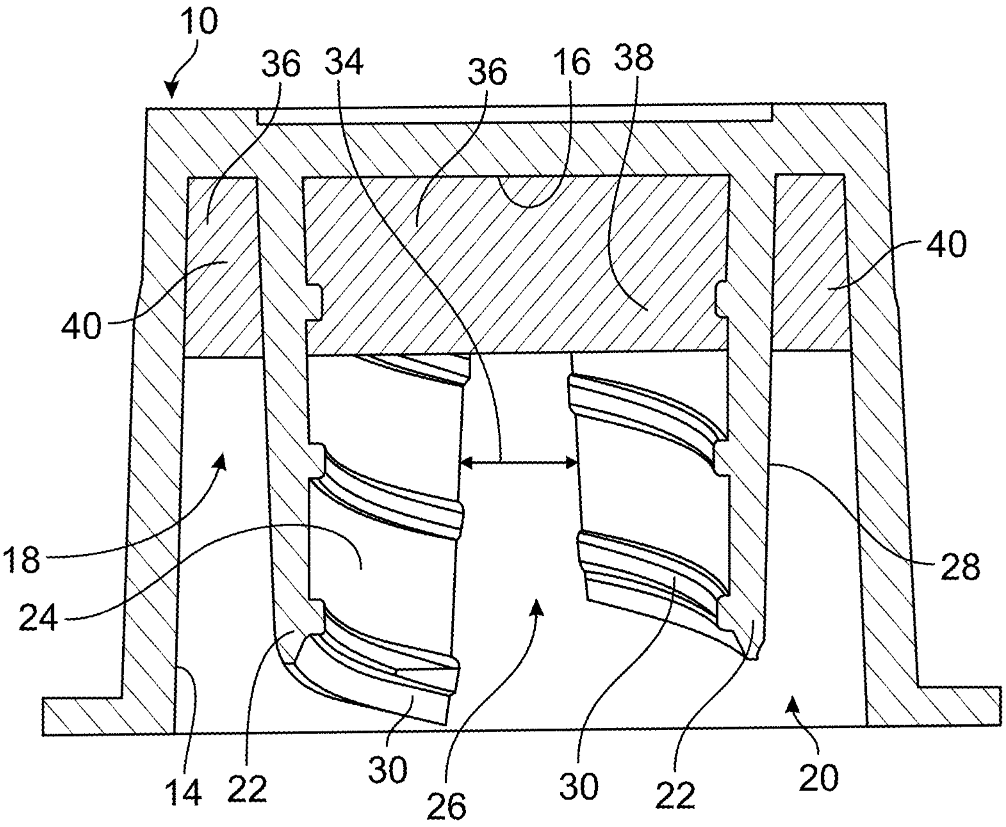
FIG. 2 (PRIOR ART)
FIG. 2 is an axial, cross-sectional view of the universal cap of FIG. 1, which corresponds to FIG. 10 of U.S. Pat. No. 11,511,100.

Embodiments of the disclosure pertain to a universal cap for connection to and disinfection of a medical connector, including male connectors and female connectors. In some embodiments, the male connectors and female connectors are threaded male and female Luer connectors. The universal cap embodiments disclosed herein facilitate easier cap alignment and engagement with threaded male or female Luer medical connectors and enhanced connector disinfection. A split-collar protrusion projects axially from a closed end wall of the cap towards the open bottom and comprises at least an opposed pair of parallel, sector-shaped, collet fingers/prongs that terminate in protrusion tips. The inner wall of each collet finger respectively defines a split-flange cantilever. Inner and outer walls of each collet finger define split threads, which are respectively sized for mating engagement with respective corresponding threads of Luer connectors. An absorbent material is oriented between the split flanges and the cap bottom. In some embodiments, the absorbent material is infused with an antimicrobial agent. As the cap is affixed to a Luer connector, compression of the absorbent material biases the split flanges toward the cap end wall and deflects the collet fingers/prongs radially inwardly, toward the cap's axial centerline, for easier cap alignment and engagement with the connector and enhanced connector disinfection. The exemplary cap disclosed herein provides a mechanical barrier for medical connectors and retains the antimicrobial agent for disinfection. The cap of the present disclosure allows the medical practitioner to streamline the disinfection process by simplifying cap/connector engagement while simultaneously disinfecting the connector.

In this disclosure, where generally applicable, a convention is generally followed wherein the distal end of the device is the end closest to a patient, and the proximal end of the device is the end away from the patient and closest to a clinician or other medical practitioner. Thus, with respect to the universal caps disclosed herein, the open end of the cap that connects to a male or female Luer connector is referred to as its distal end while the closed end of the cap is referred to as its proximal end. As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

As would be readily appreciated by skilled artisans in the relevant art, while descriptive terms such as "lock", "tip", "hub", "thread", "sponge", "prong", "protrusion", "wall", "top", "side", "bottom" and others are used throughout this specification to facilitate understanding, it is not intended to limit any components that can be used in combinations or individually to implement various aspects of the embodiments of the present disclosure.

As used herein, the term "medical device" refers to common medical devices having threaded or interlocking connections, the connections having corresponding mating elements. By way of example but not limitation, a syringe may have a male threaded connection which releasably interlocks with a secondary medical device such as a male luer connection of a catheter, an IV line and the like. The threaded connection may include a lumen defining a fluid path surrounded by a protruding wall having the threaded means for attaching to the secondary medical device.

As would be readily appreciated by skilled artisans in the relevant art, while descriptive terms such as "thread", "taper", "tab", "slant", "wall", "top", "side", "bottom" and others are used throughout this specification to facilitate understanding, it is not intended to limit any components that can be used in combinations or individually to implement various aspects of the embodiments of the present disclosure.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

Exemplary embodiments of the present disclosure provide caps that can reduce the number of device types and logistics currently needed in the hospital setting for connecting, capping, and/or disinfecting male and female threaded fluid luer connectors, by roughly half by including in a single cap or device features allowing it to be use with both male needleless connectors and female needleless connectors.

According to still further exemplary implementations of the embodiments of the present disclosure, female threads are sized and have a thread pattern that will engage with a standard ISO594-2 type of male fitting and/or male threads that are sized and have a thread pattern that will engage with a standard ISO594-2 type of female fitting. An example of an ISO594-2 type of fitting is a Q-style fitting.

In one or more embodiments, the female needless connector may be selected from the group consisting essentially of needle-free connectors, catheter luer connectors, stopcocks, and hemodialysis connectors. In one or more embodiments, the needleless connector is selected from a Q-Syte connector, MaxPlus, MaxPlus Clear, MaxZero, UltraSite, Caresite, In Vision-Plus, Safeline, OneLink, V-Link, ClearLink, NeutraClear, Clave, MicroClave, MicroClave Clear, Neutron, NanoClave, Kendall, Nexus, In Vision, Vadsite, Bionector, etc.

In one or more embodiments, the male connector may be an intravenous tubing end, a stopcock or male lock luer.

Before describing several exemplary embodiments of the disclosure, it is to be understood that the disclosure is not limited to the details of construction or process steps set forth in the following description. The disclosure is capable of other embodiments and of being practiced or being carried out in various ways.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

Figure 3:
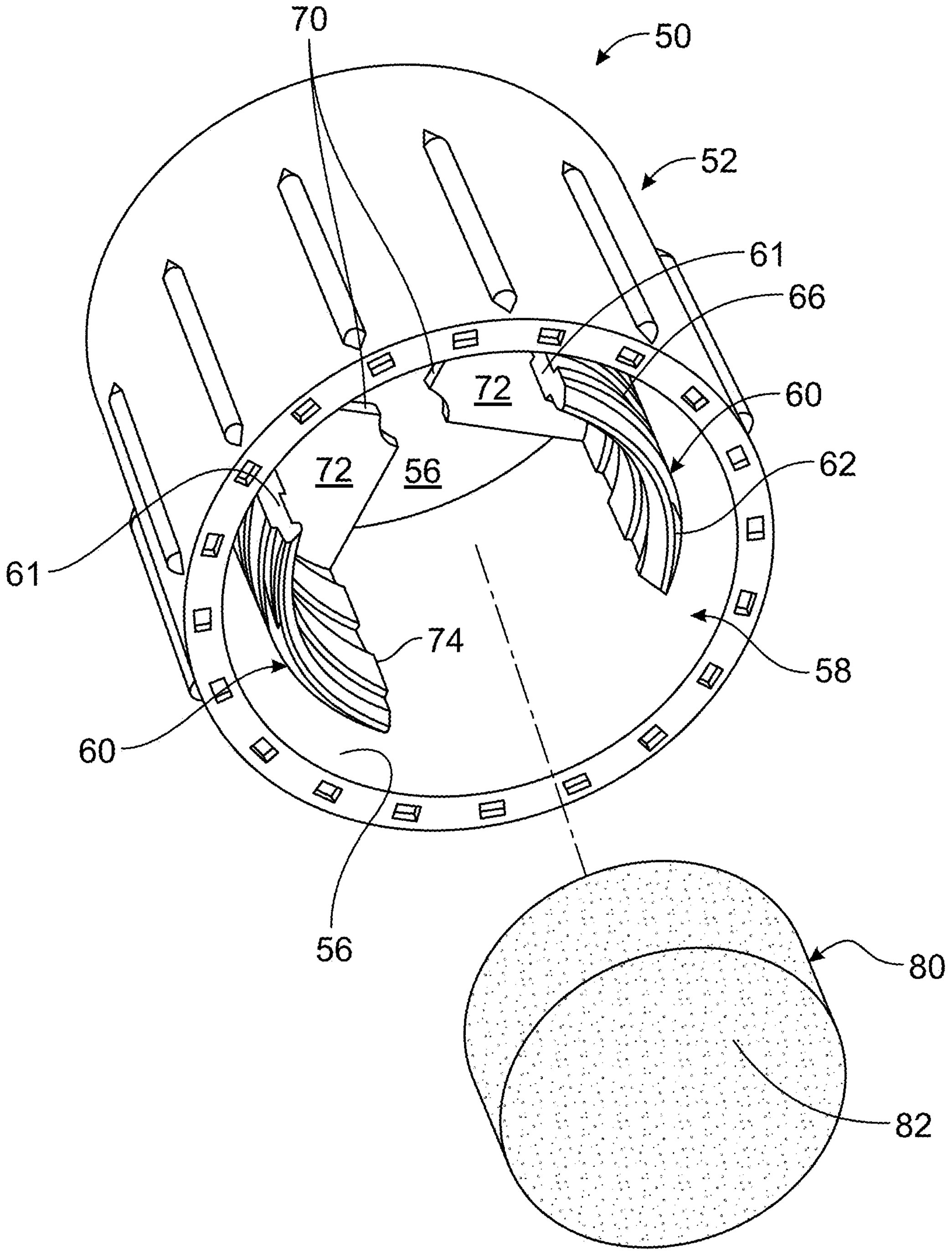
FIG. 3 is an exploded, isometric view of an embodiment of a universal cap of the present disclosure, for coupling to either male or female Luer connectors.
Figure 4:
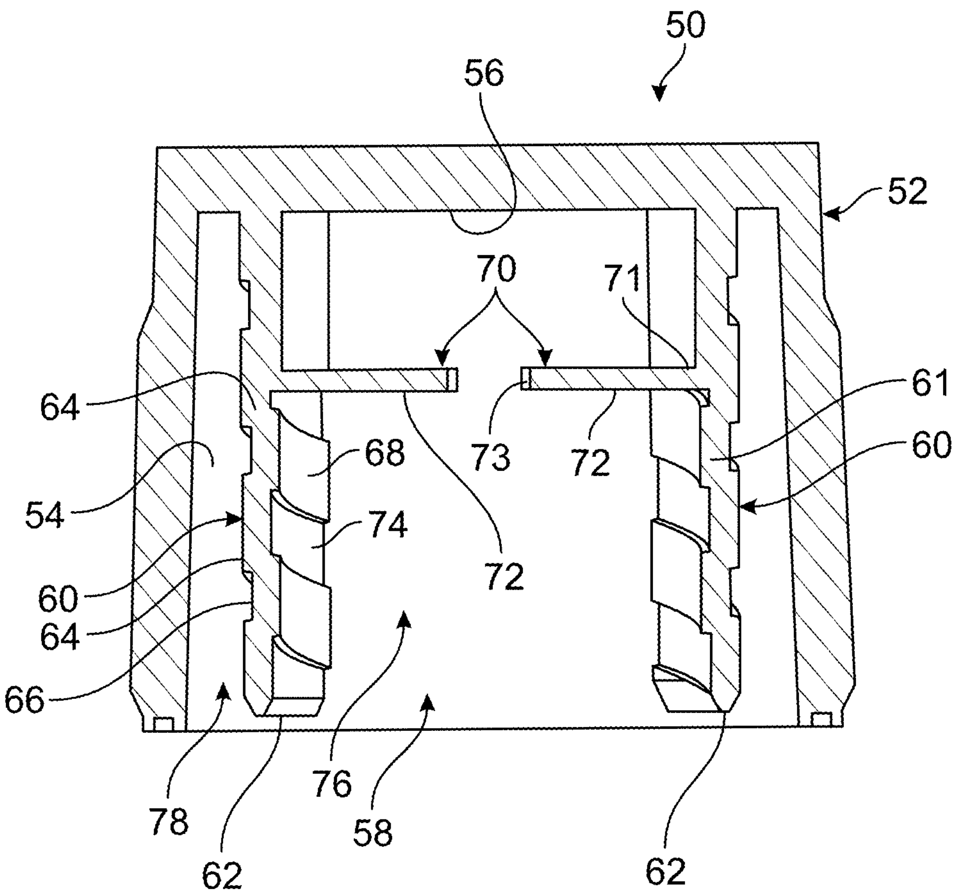
FIG. 4 is an axial, cross-sectional view of the universal cap of FIG. 3.
Figure 5:
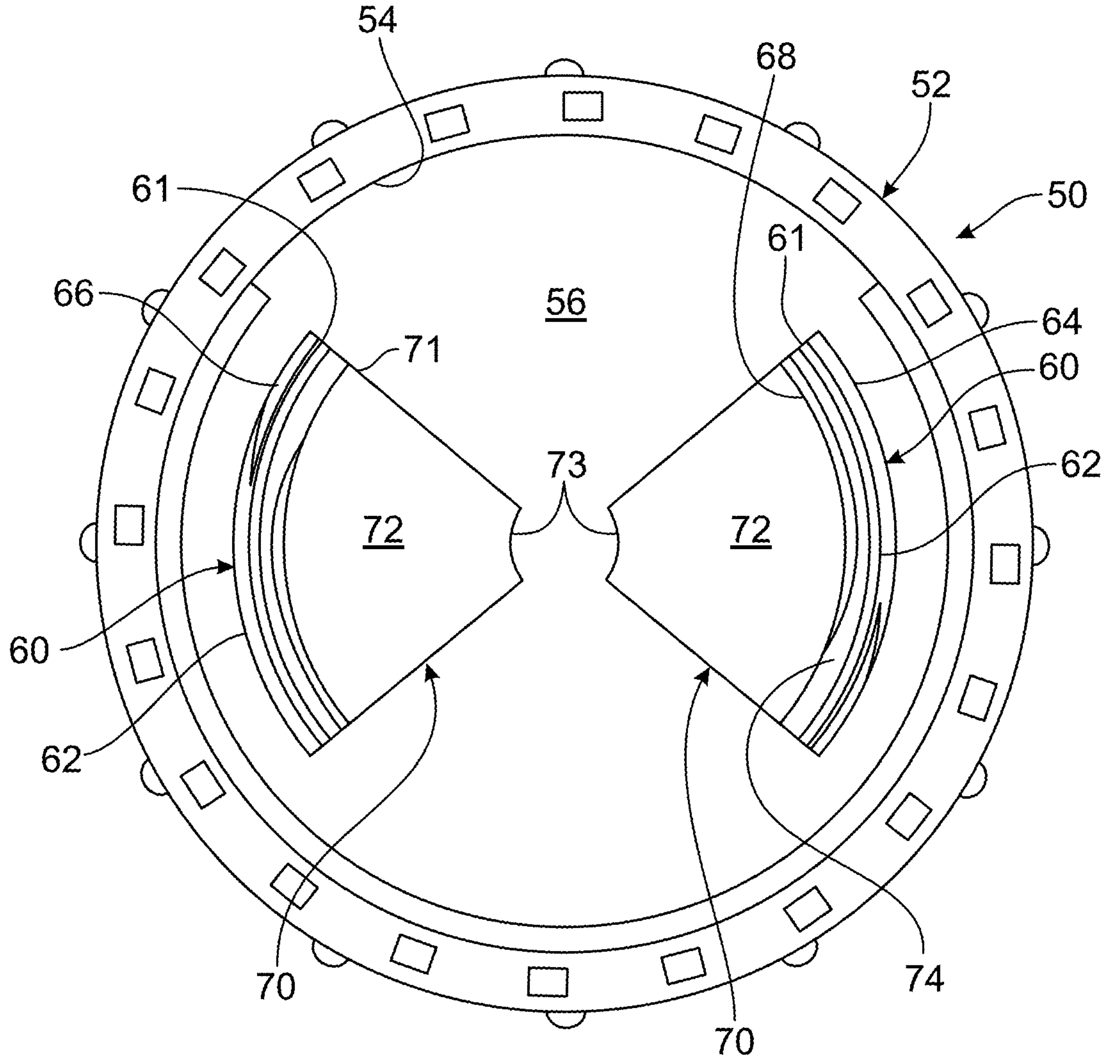
FIG. 5 is a bottom plan view of the universal cap of FIG. 3.

Referring to FIGS. 3-5, a first aspect of the present disclosure relates to a cap 50 having a housing 52 with a housing sidewall 54 and a closed top or end wall 56 on a proximal end of the housing. A distal or bottom end of the housing 52 defines an open bottom 58. A split-collar protrusion 60 projects axially from the closed top wall 56. As shown, the split collar protrusion comprises an opposed pair of parallel, sector-shaped, collet fingers 61 (also referred to herein as collet prongs), each respectively having a distal, axially oriented protrusion tip 62, a protrusion outer wall 64, and outer wall split threads 66 sized for mating engagement with corresponding collar threads of a male Luer connector. The outer wall split threads 66 start at the protrusion tip 62 and terminate proximate the top wall 56

Each collet finger/prong 61 defines a protrusion inner wall 68 and a cantilevered split flange 70. Each split flange 70 has a flange root 71 that is coupled to its corresponding protrusion inner wall 68, from which projects a distal, axial contact surface 72 that terminates in a flange tip 73. Collectively, the respective flange tips 73 of the split flanges 70 are in radially inwardly opposed orientation with respect to an axial centerline of the split-collar protrusion 60, and commonly oriented radially along the protrusion inner wall, intermediate the closed top wall 60 and the protrusion tips 62. While two collet fingers/prongs 61 are shown in this cap 50 embodiment, other embodiments incorporate more than two collet fingers.

Collectively, the collet fingers/prongs 61 define a circular platform, about an axial centerline, as shown in FIG. 5, and a generally cylindrical, protrusion outer wall 64, with the radially outwardly facing, male-Luer engageable, outer split threads 66. The inner wall 68 of each of the collet fingers 61 defines radially inwardly facing, female-Luer engageable, inner split threads 74, which start at the protrusion tip 62 and terminate before the split flange 70, proximate the top wall 56. Collectively, the protrusion inner walls 68 define an inner, cylindrical-shaped second cavity 76 and an outer, annularly shaped first cavity 78. In other embodiments, caps have a protrusion comprising any number of identical and/or different (in any dimensional characteristics, such as length width, thickness, or shape) collet fingers/prongs, as long as the protrusion is configured to engage a female connector with its inner split threads on its inner surface and engage a male connector with its outer split threads on its outer surface.

A cylindrically shaped, absorbent material 80, having a proximal axial surface 82, is interposed within the inner, second cavity 76, retained by radial compression and friction engagement with the female Luer engageable split threads 74. The absorbent material 80 abuts the axial contact surface 72 of each of the split flanges 70. In one or more embodiments, the absorbent material 80 is a nonwoven material, foam, or a sponge. In a specific embodiment, the foam is a polyurethane foam. In a specific embodiment the absorbent material 80 is in the form of a foam plug. In yet another exemplary implementation, a disinfecting member or members, such as an absorbent material 80, in the form of an IPA-soaked sponge and/or sponge.

The cap 50 can disinfect Luer connectors by integrating disinfectant or antimicrobial agent in the absorbent material 80. In some embodiments, the disinfectant or antimicrobial agent is directly included in the inner, cylindrical-shaped cavity 76 and/or the outer, annularly shaped cavity 78. In other embodiments, disinfectant or antimicrobial agent is absorbed into sponges or foam material comprising the absorbent material 80. Cap 50 is compatible in interacting with various disinfectants. In one or more embodiments, the disinfectant or antimicrobial agent includes variations of alcohol or chlorhexidine. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material 80, toward the closed end wall 56 of housing 52 upon connection to a female Luer connector or the male Luer connector allows the connector to contact the disinfectant or antimicrobial agent to disinfect the connector. Thus, compression of the absorbent material 80 while coupling the cap 50 to a Luer connector disinfects the connector.

Figure 6:
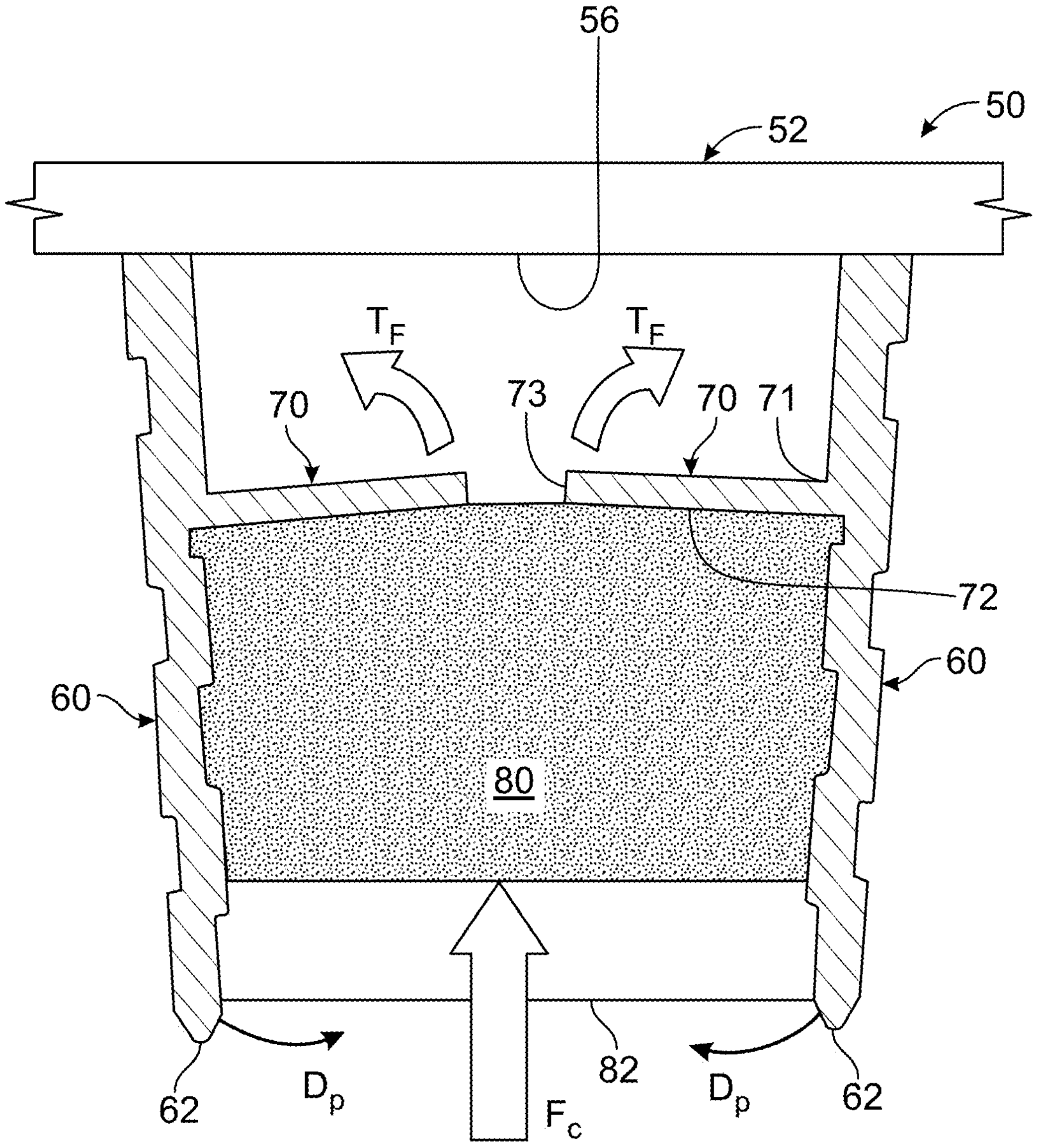
FIG. 6 is a schematic force application diagram illustrating compressive forces $F_C$ applied to the universal cap of the present disclosure in the corresponding to FIG. 4, resulting torque moments $T_F$ and radially-inwardly directed deflection $D_P$ of the cap protrusions.
Figure 7:
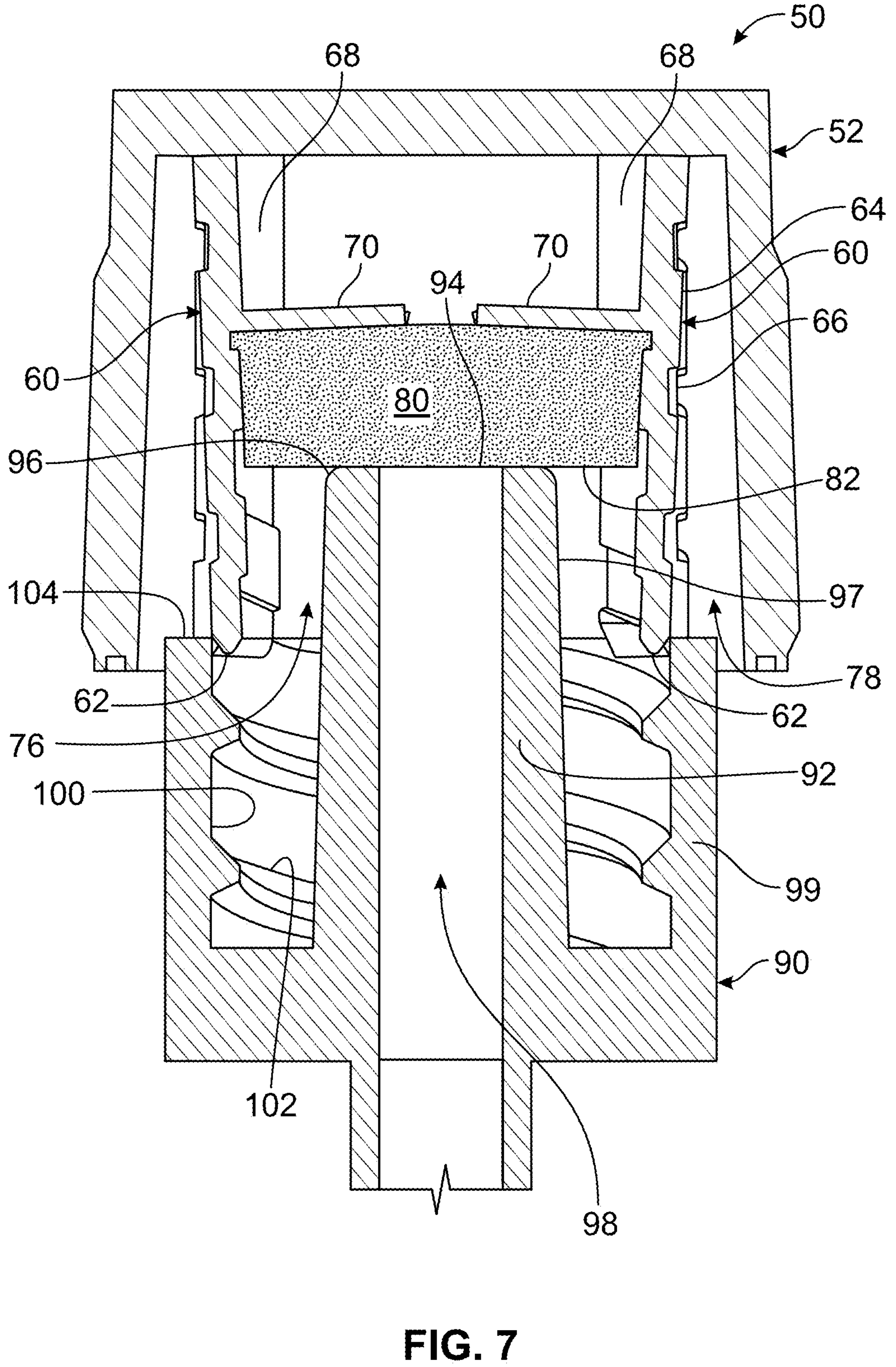
FIG. 7 is an axial, cross-sectional view of a universal cap of the present disclosure engaging a male Luer connector.
Figure 8:
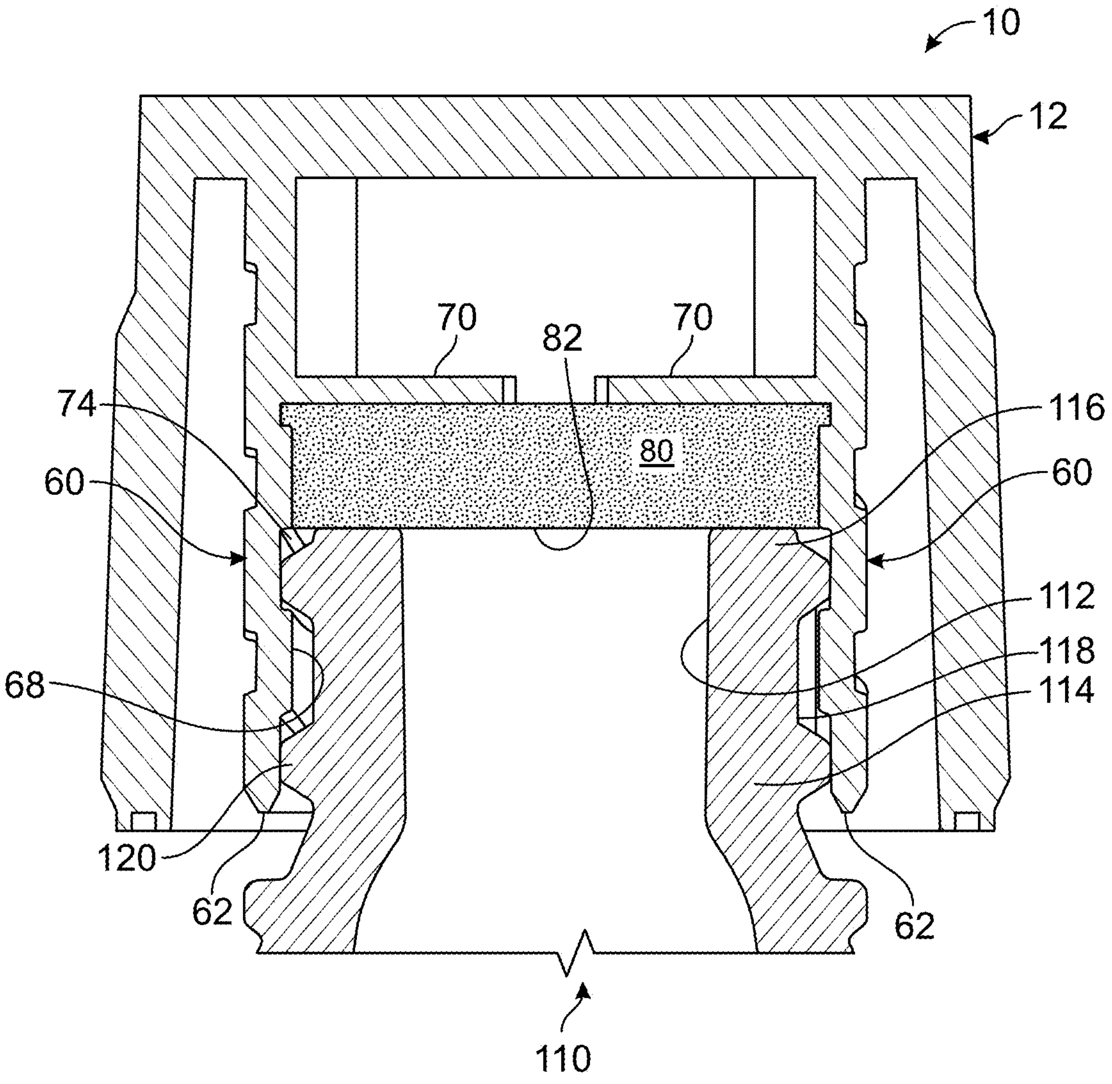
FIG. 8 is an axial, cross-sectional view of a universal cap of the present disclosure engaging a female Luer connector.

Referring to FIGS. 6-8, the cap 50 embodiment enhances alignment, threaded engagement, and disinfection of either male 90 or female 110, threaded Luer connectors as they are coupled together and compress the absorbent material (e.g., sponge) 80. FIG. 6 illustrates schematically structural deflection of the split-collar protrusion 60 in reaction to axially oriented, insertion force $F_C$ as the cap 50 is affixed to a male or female Luer connector. As the sponge 80 is compressed, the insertion force $F_C$ against the respective distal, axial contact surfaces 72 of the opposing split flanges 70, applying torque moments $T_F$ about the flange roots 71. The applied torque moments $T_F$ bias and deflect the flanges 70 and their flange tips 73 in radially outwardly directions as shown by the torque moment arrows. In reaction, the collet fingers/prongs 61 deflect radially inwardly as depicted by the deflection arrows $D_P$ so that their respective distal tips 62 are radially closer to the cap 50 axial centerline, compared to when the collet fingers are in a relaxed state, with no applied insertion force $F_C$. Advantages of the collet finger/prong 61 deflection $D_P$ in the cap 50 embodiment are illustrated in the Luer connector engagement examples shown in FIGS. 7 and 8.

In FIG. 7, the cap 50 is applied to an exemplary threaded, male Luer IV connector 90. The IV connector 90 incorporates a male Luer tip 92, having a proximate male tip 94 with a curved, rollover edge 96 that blends into a Luer-taper, circumferential outer surface 97 and a lumen 98. A collar 99 of the IV connector 90 defines a collar inner surface 100 with male Luer threads 102 and terminates in a collar proximal edge 104. During cap 50 affixation to the IV connector 90, the connector's proximate male tip 94 makes contact with the distal axial surface 82 of disinfectant sponge 80, before making contact between the distal tips 62 of the cap and the collar proximal edge 104 of the connector. This in turn, applies the axial insertion force $F_C$ load to the sponge 80, compressing the sponge. The compressed sponge transfers the axial load to the cantilever-like split flanges 70, deflecting the distal tips 62 of the collet fingers/prongs 61 and their outer wall threads 66 radially inwardly towards the axial centerline of the cap 50. With the distal tips 62 of the collet fingers/prongs 61 and their outer wall threads 66 bending inwards as a result of the sponge 80 compression, they provide radial engagement clearance between themselves and the corresponding inner surface 100 and proximal edge 104 of the collar 99 before contact engagement of the cap outer wall threads 66 and IV connector male Luer threads 102. The collet finger 61 deflection improves engagement tolerances and/or reduces interference fit between the now engageable outer wall split threads 66 of the cap 50 and the male Luer threads 102 of the IV connector 90.

In addition to improving cap 50 and male IV connector 90 engagement tolerances and/or interference fit reduction for enhanced component mating, the cap embodiments disclosed herein also enhance disinfection of the tapered, male Luer portion 92 during cap engagement. As the male IV connector is inserted within the cap 50 and the insertion force $F_C$ deflects the split flanges 70, the distal axial surface 82 of the compressing sponge 80 biases against the proximal tip 94, rollover edge 96 and upper adjoining circumferential outer surface 97 of the tapered, male Luer portion 92, scrubbing them with disinfectant retained within the sponge. As the cap 50 and the male IV connector 90 are screwed together, additional circular scrubbing action further disinfects the tapered, male Luer portion 92.

In FIG. 8, the cap 50 is applied to an exemplary threaded, female Luer IV connector 110. The female IV connector 110 has a tapered female portion 112 for complementary engagement with a corresponding male Luer connector, a sidewall 114, and a proximal tip 116. An outer surface 118 of the sidewall 114 defines female Luer threads 120. When the cap 50 is applied to the female IV connector 110, the respective mating inner wall split threads 74 of the cap and the threads 120 of the female IV connector contact and engage each other before the proximal tip 116 of the female IV connector contacts the distal axial surface 82 of the disinfectant sponge. Thus, the opposing split flanges 70 and the collet fingers 61 are in a relaxed state, allowing the cap 50 split threads 74 and the female IV connector threads 120 to mate with each other without significant frictional or radial engagement interference. As the cap 50 is tightened, compressing the sponge 80, the distal proximal tips 62 of the collet fingers/prongs 61 deflect inwardly toward the cap's axial centerline, radially compressing the mating split threads 74 and the female IV connector threads 120 relative to each other; this tightens cap and female IV connector grip.

Therefore, the same universal cap 50 of the present disclosure, with its split-collar protrusion 60, facilitates easier cap alignment, engagement with and enhanced disinfection of male Luer connectors, such as the male IV connector 90 of FIG. 7, while also enhancing disinfection of and engagement with female Luer connectors, such as the female IV connector 110 of FIG. 8. Universality of the self-aligning cap 50 provides a single disinfection and sealing solution for both male and female Luer fittings. This reduces inventory expenses and requires clinicians to be familiar with only one type of cap for all sealing and Luer fitting disinfection needs.

In various embodiments, the cap 50 of the present disclosure is constructed from any of a number of types of plastic materials such as polycarbonate, polypropylene, polyethylene, glycol-modified polyethylene terephthalate, acrylonitrile butadiene styrene or any other injection-moldable, medical-grade, plastic material used in medical devices. In one or more embodiments, the cap 50 comprises a polypropylene or polyethylene material. In some embodiments, the cap 50 is a monolithic structure. In some embodiments, the cap 50 is a monolithic structure, constructed of medical grade plastic. In some embodiments, the cap 50 is formed by an injection molding process. In some embodiments, the housing sidewall 54 and the closed top or end wall 56 of the housing 52 are of unitary construction and the split-collar protrusion 60, including collet fingers/prongs 61 are of separate, unitary construction, with both unitary components affixed to each other by heat or friction welding, adhesive or mechanical staking/fastening.

Reference throughout this specification to "one embodiment," "certain embodiments," "various embodiments." "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. A cap for coupling to a male or female Luer medical connector, comprising:

a housing having: an axial centerline, defining a first cavity formed within a housing top wall and a circumscribing housing sidewall, and an open bottom of the housing;

a split-collar protrusion within the first cavity, coupled to the housing top wall, circumscribing the axial centerline and projecting toward the open bottom, the protrusion having a plurality of opposed, parallel, sector-shaped, collet prongs, each prong respectively having: a distal protrusion tip, a protrusion outer wall surface defining outer wall split threads that are sized and adapted for mating engagement with corresponding collar threads of the male Luer connector, an inner wall surface defining inner wall split threads that are sized and adapted for mating engagement with corresponding threads of the female Luer connector, the respective inner wall split threads and the respective outer wall split threads starting at the distal protrusion tip and terminating proximate the housing top wall, the respective inner wall surfaces of the collet prongs defining a second cavity sized and adapted for receipt of the male or the female Luer connector;

a split flange coupled to the inner wall surface of each respective collet prong by a flange root, intermediate the inner wall split threads and the housing top wall, each separate, respective split flange having a distal axial contact surface that is commonly oriented radially inwardly with respect to the axial centerline of the housing and terminates in a flange tip, wherein said flange tip faces radially inwardly; and an absorbent material interposed within the second cavity, between the respective split flanges and the open bottom of the housing, the absorbent material configured to compress during advancement of the male or the female Luer connector within the second cavity and biasing the split flanges toward the top wall of the housing, the now biased split flanges deflecting the protrusion tip of its respective collet prong inwardly toward the axial centerline.

2. The cap of claim 1, upon insertion and advancement of a tapered male tip of the male Luer connector into the second cavity and configured to compress the absorbent material, the protrusion tip of each collet prong configured to deflect radially inwardly, away from a proximal edge and an inner collar surface of a collar of the male Luer connector, thereby avoiding interference contact between each protrusion tip and the collar.

3. The cap of claim 2, an adjoining proximal tip, rollover edge and circumferential outer surface of the tapered male tip of the threaded male Luer connector configured to compress the absorbent material upon insertion and threaded advancement thereof into the second cavity, and the absorbent material configured to scrub said proximal tip, rollover edge and circumferential outer surface during tightening of the outer wall split threads of the cap and the male Luer connector.

4. The cap of claim 1, upon insertion and threaded advancement of the female Luer connector into the second cavity and compressing the absorbent material, the protrusion tip of each collet prong configured to deflect radially inwardly and bias its inner wall split threads into contact with corresponding threads formed on an outer surface sidewall of the female Luer connector.

5. The cap of claim 4, the absorbent material configured to scrub a surface of a tapered female portion of the female Luer connector during tightening of the respective threads of the cap and the female Luer connector.

6. The cap of claim 1, further comprising a disinfectant or an antimicrobial agent retained within the absorbent material.

7. The cap of claim 6, wherein the disinfectant or antimicrobial agent is selected from a group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

8. The cap of claim 7, wherein the disinfectant or antimicrobial agent is a fluid or a gel.

9. The cap of claim 6, wherein the disinfectant or antimicrobial agent is a fluid or a gel.

10. The cap of claim 1, wherein the absorbent material is a foam or a polyurethane foam, or a sponge.

11. The cap of claim 1, the split-collar protrusion comprising a pair of collet prongs and split flanges.

12. The cap of claim 11, the cap comprising a monolithic structure.

13. The cap of claim 12, the monolithic structure of the cap formed by injection molding the cap.

* * * * *